(12) United States Patent
Capone et al.

(10) Patent No.: US 9,084,740 B2
(45) Date of Patent: Jul. 21, 2015

(54) METHODS AND COMPOSITIONS FOR IMPROVING APPEARANCE AND FORMATION OF SCAR TISSUE

(71) Applicant: Johnson & Johnson Consumer Companies, Inc., Skillman, NJ (US)

(72) Inventors: Kimberly Capone, Lambertville, NJ (US); Euen Thomas Graham Ekman Gunn, Hopewell, NJ (US); Diana Roshek Johnson, North Brunswick, NJ (US); Russel Walters, Philadelphia, PA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 14/182,427

(22) Filed: Feb. 18, 2014

(65) Prior Publication Data

US 2014/0234249 A1   Aug. 21, 2014

Related U.S. Application Data

(60) Provisional application No. 61/766,292, filed on Feb. 19, 2013, provisional application No. 61/777,059, filed on Mar. 12, 2013.

(51) Int. Cl.

| | | |
|---|---|---|
| A61K 9/00 | (2006.01) | |
| A61K 8/81 | (2006.01) | |
| A61Q 19/00 | (2006.01) | |
| A61L 15/22 | (2006.01) | |
| A61L 26/00 | (2006.01) | |
| A61Q 19/06 | (2006.01) | |

(52) U.S. Cl.
CPC ............. *A61K 8/8152* (2013.01); *A61L 15/22* (2013.01); *A61L 26/008* (2013.01); *A61L 26/0009* (2013.01); *A61L 26/0076* (2013.01); *A61Q 19/00* (2013.01); *A61Q 19/06* (2013.01)

(58) Field of Classification Search
CPC .......................... A61K 9/0019; A61K 8/8152
USPC ......................................................... 424/401
See application file for complete search history.

(56) References Cited

U.S. PATENT DOCUMENTS

| | | | |
|---|---|---|---|
| 3,755,560 | A | 8/1973 | Dickert et al. |
| 4,384,096 | A | 5/1983 | Sonnabend |
| 4,421,769 | A | 12/1983 | Dixon et al. |
| 4,883,864 | A | 11/1989 | Scholz |
| 4,943,624 | A | 7/1990 | Regen |
| 5,179,190 | A | 1/1993 | Regen |
| 5,372,807 | A | 12/1994 | Poiani et al. |
| 5,874,495 | A | 2/1999 | Robinson |
| 5,955,883 | A | 9/1999 | Hennig |
| 6,060,474 | A * | 5/2000 | Williams et al. ......... 514/253.08 |
| 6,268,126 | B1 | 7/2001 | Neenan et al. |
| 6,433,061 | B1 | 8/2002 | Marchant et al. |
| 6,890,553 | B1 | 5/2005 | Sun et al. |
| 7,084,104 | B2 | 8/2006 | Martin et al. |
| 7,098,180 | B2 | 8/2006 | Ganopolsky et al. |
| 7,157,414 | B2 | 1/2007 | Librizzi et al. |
| 7,179,475 | B1 | 2/2007 | Burnett et al. |
| 7,754,666 | B2 | 7/2010 | Walters et al. |
| 7,754,667 | B2 | 7/2010 | Walters et al. |
| 7,772,421 | B2 | 8/2010 | Yang et al. |
| 7,803,403 | B2 | 9/2010 | Librizzi et al. |
| 7,906,475 | B2 | 3/2011 | Walters et al. |
| 8,025,902 | B2 | 9/2011 | Librizzi et al. |
| 8,071,674 | B2 | 12/2011 | Yang et al. |
| 8,211,850 | B2 | 7/2012 | Andjelic et al. |
| 8,338,348 | B2 | 12/2012 | Anim-Danso et al. |
| 2006/0228348 | A1 | 10/2006 | Stefano |
| 2008/0182780 | A1 | 7/2008 | Linge et al. |
| 2010/0008938 | A1 | 1/2010 | Diwan et al. |
| 2010/0256089 | A1 | 10/2010 | Maguire et al. |
| 2011/0041611 | A1 | 2/2011 | Hofer et al. |
| 2011/0082105 | A1 | 4/2011 | Fevola et al. |
| 2011/0319306 | A1 | 12/2011 | Walters et al. |
| 2011/0319307 | A1 | 12/2011 | Gunn et al. |
| 2011/0319308 | A1 | 12/2011 | Gunn et al. |
| 2012/0321574 | A1 | 12/2012 | Burnett et al. |

FOREIGN PATENT DOCUMENTS

| | | |
|---|---|---|
| EP | 226097 B | 5/1990 |
| EP | 384532 A | 8/1990 |
| EP | 759301 A | 2/1997 |
| EP | 705852 A | 9/2010 |
| EP | 2402000 A | 1/2012 |
| EP | 2468246 A | 6/2012 |
| WO | WO 98/03572 A | 1/1998 |
| WO | WO 03/051326 A1 | 6/2003 |
| WO | WO 2005/105115 A1 | 11/2005 |
| WO | WO 2008/131260 A | 10/2008 |

(Continued)

OTHER PUBLICATIONS

Fletcher, et al., "Candidate polyanion microbicides inhibit HIV-1 infection and dissemination pathways in human cervical explants", *Retrovirology* (2006), vol. 3, Issue 46.
Jenkins, A.D. et al., Glossary of Basic Terms in Polymer Science, Pure Appl. Chem. vol. 68, No. 12, pp. 2287-2311 (1996).
McCutcheon's Detergents and Emulsifiers, North American Edition (1986), pp. 317-324.
Invittox Protocol No. 86 (May 1994), the Trans-epithelial Permeability (TEP) Assay.
Kadouch, D. J. et al., "Postoperative pressure therapy of ear keloids using a custom-made methyl methacrylate stent", Dermatologic Surgery: Official Publication for American Society for Dermatologic Surgery [et al.], Mar. 2010, vol. 36, No. 3, pp. 383-385, XP002722922, ISSN: 1524-4725.
Kasermann, et al., "Inactivation of enveloped ciruses by singlet oxygen thermally generated from a polyeric naphthalene derivative", *Antiviral Research* (Apr. 1998) vol. 38, No. 1, pp. 55-62.

(Continued)

*Primary Examiner* — Gina Justice

(57) ABSTRACT

This invention relates to methods and compositions for degrading collagen in mammalian skin, thereby improving the appearance and/or reducing the size of a closed wound, which may be a scar or a keloid and cellulite or other conditions wherein excessive collagen is a problem.

3 Claims, No Drawings

(56) References Cited

FOREIGN PATENT DOCUMENTS

| WO | WO 2010/131032 A2 | 11/2010 |
| --- | --- | --- |
| WO | WO 2011/107440 A1 | 9/2011 |
| WO | WO 2012/004669 A | 1/2012 |

OTHER PUBLICATIONS

Matsumura et al., "Amphipathic DNA Polymers Inhibit Hepatitis C Virus Infection by Blocking Viral Entry", *Gastroenterology* (Aug. 1, 2009) vol. 137, No. 2, pp. 673-681 (Elsevier, Philadelphia, PA).

Neurath et al., "Anti-HIV-1 activity of anionic polymers: a comparative study of candidate microbicides", *BMC Infectious Diseases* (2002), vol. 2, Issue 27.

Sagarin, Cosmetics, Science and Technology, 2nd Edition, vol. 1 (1972), pp. 32-43 and 72-73.

Stefanovic, L. et al., "Inhibitory effect of dicationic diphenylfurans on production of type I collagen by human fibroblasts and activated hepatic stellate cells", Life Sciences, Pergamon Press, Oxford, GB, vol. 76, No. 17, Mar. 11, 2005, pp. 2011-2026, XP027713229, ISSN: 0024-3205 [retrieved on Mar. 11, 2005].

Wenninger and McEwen eds., the International Cosmetic Ingredient Dictionary and Handbook (The Cosmetic, Toiletry and Fragrance Assoc., Washington D.C., 7th Edition 1997), pp. 1626, 1650-1667, 1673-1686, and 1693-1697.

Stuart et al., "Collagen-Binding Peptidoglycans Inhibit MMP Mediated Collagen Degradation and Reduce Dermal Scarring", PLoS One 6(7):1-8, 2011.

\* cited by examiner

METHODS AND COMPOSITIONS FOR IMPROVING APPEARANCE AND FORMATION OF SCAR TISSUE

CROSS REFERENCE TO RELATED APPLICATIONS

This application claims priority of the benefit of U.S. Provisional Application Ser. No. 61/766,292 filed Feb. 19, 2013 and U.S. Provisional Application Ser. No. 61/777,059 filed Mar. 12, 2013 and is related to copending U.S. patent application Ser. No. 14/182,439, filed Feb. 18, 2014 The complete disclosures of the aforementioned related U.S. patent applications are hereby incorporated by reference for all purposes.

FIELD OF THE APPLICATION

This invention relates to methods and compositions for degrading collagen in mammalian skin, thereby improving the appearance and/or reducing the size of a closed wound, which may be a scar or a keloid and cellulite or other conditions wherein excessive collagen is a problem.

BACKGROUND OF THE APPLICATION

A scar forms in response to cutaneous injury as part of the natural wound healing process. It is a lengthy and continuous process, although it is typically recognized as occurring in stages. The wound healing process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage the previously constructed and randomly organized matrix is remodeled into an organized structure that is highly cross-linked and aligned to increase mechanical strength.

The changing patterns of the connective tissue matrix during repair following injury require a delicate balance between synthesis and degradation of collagen and proteoglycans. Under normal circumstances this balance is maintained, while in many diseased states, it is altered, leading to an excessive deposition of collagen, to a loss of functional tissue, or to disfigurement. With hypertrophic scars and keloids, the biosynthetic phase continues longer than necessary to repair the wound. In order to maintain nutrient supply, vascular in-growth occurs, resulting in large, highly vascularized scars which are unsightly and can be disabling. Keloids and hypertrophic scars result in functional and cosmetic deformity. They are a common clinical problem.

While the histological features characterizing hypertrophic scars have been well documented, the underlying pathophysiology is not well known. Hypertrophic scars are a side effect of excessive wound healing, and generally result in the overproduction of cells, collagen, and proteoglycans. Hypertrophic scars are thick and take the form of a raised scar on the skin as a result of overproduction of cells, collagen, and proteoglycans.

A keloid is a raised scar that exceeds the boundaries of the initial injury (unlike hypertrophic scars which typically stay within the wound boundaries), and is rarely corrected by surgical intervention. Keloids are typically characterized as tumors consisting of highly hyperplastic masses that occur in the dermis and adjacent subcutaneous tissue in susceptible individuals, most commonly following trauma. Keloids may grow into a firm lump that is many times larger than the original scar and are typically fibrotic growths that contain a collection of atypical fibroblasts and an increased abundance of extracellular matrix components, especially collagen.

Keloids are often more severe than hypertrophic scars, since they tend to invade normal adjacent tissue, while hypertrophic scars tend to remain confined within the original scar border.

Although commonly benign, hypertrophic scars and keloids often cause discomfort, pain, pruritus, physical disfigurement and impaired quality of life.

Most of the scar reduction products contain silicone in a sheet or gel format, and onion extracts (Mederma Skin Care products). It usually takes over 3 months to see some effect, because these products do not contain effective active ingredient such as any form of collagenase which targets the cause of scar formation. See www.mederma.com/learning/caring_for_scars.

Other attempts to treat hypertrophic scars and keloids include surgery, mechanical pressure, steroids, x-ray irradiation and cryotherapy. There are many disadvantages associated with each of these methods. Surgical removal of the scar tissues is often incomplete and can result in further development of hypertrophic scars and keloids at the incision and suture points. Steroid treatments are unpredictable and often result in depigmentation of the skin. X-ray therapy is the only predictable effective treatment to date; however, because of its potential for causing cancer, it is not generally recommended or accepted. The most common approach to controlling scar, and in particular excessive scar formation, is to apply pressure, which appears to be somewhat effective in many instances. This treatment has limited application, generally based on the size and location of the scar tissue on the body. Other commonly used treatments are application of Vitamin E and corticosteroids.

SUMMARY OF THE INVENTION

This invention relates to a method of improving the appearance of and/or substantially reducing the formation of scars and other visible effects of healed wounds and cellulite, including keloids and hypertrophic scars, comprising, consisting essentially of and consisting of contacting collagen contained within said scar tissue or wound with an anti-viral composition comprising at least one low molecular weight hydrophobically modified polymer in an amount effective to degrade said collagen. We envision the methods and compositions of this invention to include the treatment of any condition that would benefit by the treatment mode of degrading or destroying collagen.

Surprisingly, we have found that low concentrations of certain low molecular weight hydrophobically modified polymers known for their gentle properties are able successfully to degrade collagen located in or around the skin, in particular, in the epithelial layers of the skin. Such polymers also are capable of degrading collagen in extracellular matrix, such as that formed in connection with wound healing and in conjunction with cellulite.

DETAILED DESCRIPTION OF THE PREFERRED EMBODIMENTS

One of the methods of this invention relates to a method and composition for treating a closed wound having scar tissue on a skin surface of a mammalian subject. Such scar tissue may include a hypertrophic scar and/or a keloid scar.

Preferably, a method of administering the compositions of this invention comprise, consist essentially of and consist of injecting a composition containing a low molecular weight hydrophobically modified polymer (low MW HmP) into a scar that has formed over a closed wound.

In another embodiment, it is proposed that the composition may be applied to an open wound prior to scar formation. A composition according to this invention may be applied topically directly to the site of the wound or as part of a bandage, which is placed onto the wound.

Preferably the compositions of this invention contain at least one low MW HmP and an aqueous solvent. The solvent may be any non-irritating solvent such as deionized water and phosphate buffered saline (PBS), which is acceptable for injection into the scar. In another embodiment, the composition may be a topical composition appropriate for dispensing directly to the surface of the skin, such as a lotion or a cream as described below.

The compositions of this invention may be deployed to devices that can be applied to skin, including adhesive hydrogel bandages, injectable compositions, kits and methods for ameliorating the formation of scars and/or keloids at a wound site by degrading collagen.

As used herein, the term "wound" means is a type of injury in which skin is torn, cut or punctured (an open wound), or where blunt force trauma causes a contusion (a closed wound).

As used herein, the term "closed wound" may include a hypertrophic scar, keloid, Dupuytren's contracture, fibrotic scar or a reactive scar and the like.

Preferably, when treating scarring of a healed and/or closed wound, the method of this invention comprises, consists essentially of and consists of injecting a composition according to this invention into the scar tissue. Preferably, the composition should be placed below the layer of the stratum corneum, the outmost layer of the skin.

Preferably, the injectable compositions of this invention contain at least about 0.1% low molecular weight hydrophobically modified polymer and preferably at least about 50% solvent including suspensions, colloids, hydrogels, and emulsions, for example, water or water-propylene glycol mixtures. Such compositions may be prepared as injectables, either as liquid solutions or suspensions. Solid forms suitable for dissolving in a hydrogel or a liquid solution, or for suspending in liquid prior to use, can also be prepared. The preparation can also be emulsified. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. Details on techniques for formulation and administration may be found in the latest edition of *Remington's Pharmaceutical Sciences* (Maack Publishing Co., Easton, Pa.).

For topical administration methods, preferably, a composition containing at least about 0.1% low molecular weight hydrophobically modified polymer and preferably at least about 50% solvent including deionized water and phosphate buffer solution may be incorporated into a bandage or applied directly to the surface of the wound.

Penetration enhancers/solvents suitable for use in the present invention are alcohols, including, but not limited to, ethanol, propylene glycol, or a combination thereof. Suitable humectants/solvents for use herein, include, but are not limited to, polyethylene glycol, glycerin, sorbitol, xylitol or any combination of any of the foregoing. Suitable anhydrous vehicles for use herein include, but are not limited to, alcohols which may be the same as or different than the alcohol penetration enhancer. Non-limiting examples of such alcohols are isobutanol and isopropyl alcohol. Mechanical penetration enhancers may also be utilized. Penetration enhancing methods may be found in U.S. Pat. Nos. 7,879,823, 7,179,475, 6,890,553 and U.S. Patent Publication No. 2012/0321574, which are hereby incorporated herein by reference.

As used herein, the term "surfactant" is a surface active agent, or a substance that, when dissolved in water or an aqueous solution, reduces its surface tension or the interfacial tension between it and another liquid.

Polymeric Material

Examples of polymeric materials useful in the compositions and methods of this invention include low-molecular weight acrylic, other ethylenically-unsaturated polymers, polyesters, polycarbonates, polyanhydrides, polyamides, polyurethanes, polyureas, polyimides, polysulfones, polysulfides, combinations of two or more thereof, and the like. Examples of suitable low molecular weight acrylic polymers include hydrophobically-modified acrylic, polysaccharide, cellulose, starch polymers, combinations of two or more thereof, and the like. Suitable low molecular weight acrylic polymers include hydrophobically-modified acrylic polymers, as well as other acrylic polymers, any of which may be formed via solution, suspension, precipitation, dispersion, emulsion, inverse emulsion, microemulsion, micellar polymerization methods, and combinations of two or more thereof. The acrylic polymers for use in the present invention may be derived from any one or more monomers selected from the group consisting of (meth)acrylates, (meth)acrylamides, vinyl ethers, esters, and amides, allyl ethers, esters, amines, and amides, itaconates, crotonates, styrenics, and olefins. The acrylic polymers may be nonionic hydrophilic, nonionic hydrophobic, anionic, cationic, zwitterionic, nonassociative macromer, associative macromer, or multifunctional/crosslinking.

As used herein the term "low molecular weight" polymer refers to a polymer having a number average molecular weight ($M_n$) of about 100,000 or less as measured by gel permeation chromatography (GPC) calibrated with a poly (methyl methacrylate) (PMMA) standard. In certain preferred embodiments, low-molecular weight polymers are those having molecular weight ranges of from about 5,000 to about 80,000 $M_n$, more preferably from about 10,000 to about 50,000 $M_n$, and more preferably between about 15,000 and 40,000 $M_n$.

Certain hydrophobically-modified polymers and methods of making such polymers are described in U.S. Pat. No. 6,433,061, issued to Marchant et al. and incorporated herein by reference. The polymeric materials useful in the composition of this invention are preferably non-crosslinked, linear acrylic copolymers that are very mild to the skin and mucosa. These non-crosslinked, linear polymers are preferably of low molecular weight having a number average molecular weight of 100,000 or less as measured by gel permeation chromatography (GPC) calibrated with a poly(methyl methacrylate)

(PMMA) standard (as used herein, unless otherwise specified, all number average molecular weights ($M_n$) refer to molecular weight measured in such manner). Thus, the polymeric material functions as a copolymeric compound. The copolymeric compound is polymerized from at least two monomeric components. The first monomeric component is selected from one or more α,β-ethylenically unsaturated monomers containing at least one carboxylic acid group. This acid group can be derived from monoacids or diacids, anhydrides of dicarboxylic acids, monoesters of diacids, and salts thereof. The second monomeric component is hydrophobically modified (relative to the first monomeric component) and is selected from one or more α,β-ethylenically unsaturated non-acid monomers containing a $C_1$ to $C_9$ alkyl group, including linear and branched $C_1$ to $C_9$ alkyl esters of (meth)acrylic acid, vinyl esters of linear and branched $C_1$ to $C_{10}$ carboxylic acids, and mixtures thereof. In one aspect of the invention the second monomeric component is represented by the formula:

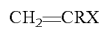

wherein R is hydrogen or methyl; X is —C(O)OR$^1$ or —OC(O)R$^2$; R$^1$ is linear or branched $C_1$ to $C_9$ alkyl; and R$^2$ is hydrogen or linear or branched $C_1$ to $C_9$ alkyl. In another aspect of the invention R$^1$ and R$^2$ is linear or branched $C_1$ to $C_8$ alkyl and in a further aspect R$^1$ and R$^2$ are linear or branched $C_2$ to $C_5$ alkyl.

Thus, preferably the hydrophobically modified polymers useful in the compositions and methods of this invention comprise, consist essentially of and consist of a low molecular weight, non-crosslinked, linear acrylic copolymer derived from at least one first monomeric component selected from the group consisting of (meth)acrylic acid and at least one second monomeric component selected from the group consisting of one or more $C_1$ to $C_9$ alkyl (meth)acrylates, wherein the low molecular weight copolymer has a number average molecular weight of about 100,000 or less.

Exemplary first monomeric components include (meth)acrylic acid, itaconic acid, citraconic acid, maleic acid, fumaric acid, crotonic acid, aconitic acid, and mixtures thereof. Exemplary second monomeric components include ethyl (meth)acrylate, butyl (meth)acrylate, 2-ethylhexyl (meth)acrylate, vinyl formate, vinyl acetate, 1-methylvinyl acetate, vinyl propionate, vinyl butyrate, vinyl 2-ethylhexanoate, vinyl pivalate, vinyl neodecanoate, and mixtures thereof. As used herein, the terms "(meth)acrylic" acid and "(meth)acrylate" are meant to include the corresponding methyl derivatives of acrylic acid and the corresponding alkyl acrylate For example, "(meth)acrylic" acid refers to acrylic acid and/or methacrylic acid and "(meth)acrylate" refers to alkyl acrylate and/or alkyl methacrylate.

More preferably, said first monomeric component is selected from the group consisting of (meth)acrylic acid and said second monomeric component is selected from the group consisting of at least one $C_1$ to $C_9$ alkyl (meth)acrylate.

The non-crosslinked, linear acrylic copolymer compounds useful in the compositions and methods of this invention can be synthesized via free radical polymerization techniques known in the art. In one aspect of the invention, the weight ratio of the first monomeric component to the second monomeric component utilized ranges from about 20:80 to about 50:50. In another aspect the weight ratio of the first monomeric component to the second monomeric component is about 35:65, and in a further aspect the weight ratio of first monomeric component to second monomeric component is about 25:75.

Methods of synthesizing the polymers useful in the compositions and methods of this invention may be found in U.S. Pat. No. 6,433,061 which is hereby incorporated herein by reference.

The linear copolymeric materials useful in the methods and compositions of this invention preferably have a viscosity of 500 mPa·s or less (Brookfield RVT, 20 rpm, spindle no. 1) at a 5 wt. % polymer solids concentration in deionized water and neutralized to pH 7 with an 18 wt. % NaOH solution. The viscosity can range from about 1 to about 500 mPa·s in another aspect, from about 10 to about 250 mPa·s in a further aspect, and from about 15 to about 150 mPa·s in a still further aspect.

Preferably, the low molecular weight, non-crosslinked linear acrylic copolymer present in the compositions and methods of this invention is potassium acrylates copolymer.

The low molecular weight hydrophobically modified polymers useful in the compositions and methods of this invention are preferably present in said compositions in amounts that are effective to inhibit, interfere with or degrade the collagen matrix in a wound healing model. Accordingly, the compositions and methods of this invention degrade collagen and would therefore prevent the formation of keloid and hypertrophic scars.

Preferably, they should be present in the compositions of this invention in an amount of from about 0.1% to about 100% percent by weight of the composition. More preferably, they should be present in the compositions of this invention in an amount of from about 0.1% to about 10% percent by weight of the composition. Even more preferably, they should be present in the amount of from about 0.1% to about 5% by weight of the composition. More preferably, they should be present in the amount of from about 0.1% to about 0.5% by weight of the composition. Most preferably, they should be present in the amount of from about 0.1% to about 0.5% by weight of the composition.

For injectible applications, the low MW HmP may be dissolved in phosphate buffered saline (abbreviated PBS). PBS is a buffer solution commonly used in biological research. It is a water-based salt solution containing sodium chloride, sodium phosphate, and, in some formulations, potassium chloride and potassium phosphate. The buffer's phosphate groups help to maintain a constant pH. The osmolarity and ion concentrations of the solution usually match those of the human body (isotonic). The preparation of a pharmacological composition that contains active ingredients dissolved or dispersed therein is well understood in the art and need not be limited based on formulation. Liquid preparations include solutions, suspensions, colloids, hydrogels, and emulsions, for example, water or water-propylene glycol mixtures. Such compositions may be prepared as injectables, either as liquid solutions or suspensions. Solid forms suitable for dissolving in a hydrogel or a liquid solution, or for suspending in liquid prior to use, can also be prepared. The preparation can also be emulsified. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. Details on techniques for formulation and administration may be found in the latest edition of *Remington's Pharmaceutical Sciences* (Maack Publishing Co., Easton, Pa.).

The compositions of this invention may be in the form of a lotion or liquid capable of being applied on the surface of the skin or on an inanimate surface that has a wound. It may also be a composition which is applied directly to the skin or contained in an adhesive bandage (i.e., the treatment solution is contained with the absorbent portion of the bandage) and placed onto the skin surface having the wound. These types of composition may be more viscous and may be based on a gel or hydrogel composition.

The compositions of this invention may be made into a wide variety of product types that include but are not limited to liquids, lotions, creams, gels, sticks, sprays, shaving creams, ointments, cleansing liquid washes and solid bars, shampoos, pastes, powders, mousses, wipes, patches, wound dressing and adhesive bandages, hydrogels and films. These product types may contain several types of cosmetically acceptable topical carriers including, but not limited to solutions, emulsions (e.g., microemulsions and nanoemulsions), gels, solids and liposomes. The following are non-limiting examples of such carriers. Other carriers may be formulated by those skilled in the art of formulating such product types.

The topical compositions useful in the methods of this invention may be formulated as solutions. Solutions preferably contain an aqueous solvent (e.g., from about 50% to about 99.99% or from about 90% to about 99% of a cosmetically acceptable aqueous solvent).

Topical compositions useful in the methods of this invention may be formulated as a solution containing an emollient. Such compositions preferably contain from about 2% to about 50% of an emollient(s). As used herein, "emollients" refer to materials used for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7$^{th}$ Edition, 1997) (hereinafter "ICI Handbook") contain numerous examples of materials for use in the compositions and methods of this invention.

A lotion may also be made from such a solution. Lotions preferably contain from about 1% to about 20% (more preferably, from about 5% to about 10%) of an emollient(s) and from about 50% to about 90% (more preferably, from about 60% to about 80%) of water.

Another type of product that may be formulated from a solution is a cream. A cream preferably contains from about 5% to about 50% (more preferably, from about 10% to about 20%) of an emollient(s) and from about 45% to about 85% (more preferably from about 50% to about 75%) of water.

Yet another type of product that may be formulated from a solution is an ointment. An ointment may contain a simple base of animal or vegetable oils or semi-solid hydrocarbons. An ointment may preferably contain from about 2% to about 10% of an emollient(s) plus from about 0.1% to about 2% of a thickening agent(s). A more complete disclosure of thickening agents or viscosity increasing agents useful herein may be found in Sagarin, Cosmetics, Science and Technology, 2nd Edition, Vol. 1, pp. 72-73 (1972) and the ICI Handbook pp. 1693-1697.

The topical compositions useful in the methods of this invention may also be formulated as emulsions. If the carrier is an emulsion, preferably from about 1% to about 10% (e.g., from about 2% to about 5%) of the carrier contains an emulsifier(s). Emulsifiers may be nonionic, anionic or cationic. Suitable emulsifiers are set forth in, for example, U.S. Pat. Nos. 3,755,560, 4,421,769, McCutcheon's Detergents and Emulsifiers, North American Edition, pp. 317-324 (1986) and the ICI Handbook, pp. 1673-1686, which are incorporated herein by reference.

Lotions and creams may also be formulated as emulsions. Preferably such lotions contain from 0.5% to about 5% of an emulsifier(s). Such creams would preferably contain from about 1% to about 20% (more preferably, from about 5% to about 10%) of an emollient(s); from about 20% to about 80% (more preferably, from 30% to about 70%) of water; and from about 1% to about 10% (more preferably, from about 2% to about 5%) of an emulsifier(s).

Other compositions useful in the methods of this invention include gels and liquid compositions that may be applicable to mucosal surfaces for inhibiting viral transmission. Mucosal surfaces include but are not limited to the vagina, rectum, nasal passages, mouth and throat. Preferably, such compositions should include at least one polyhydric alcohol, including glycerin, polyethylene glycol, propylene glycol, sorbitol or a combination thereof. Other polyhydric alcohols know to those of ordinary skill in the art may be used in the compositions and methods of this invention, including polyethylene glycols ranging from molecular weight of from about 300 to about 1450. Preferably, there should be from about 0.1 to about 50% by weight of glycerin and from about 2 to about 40% by weight of propylene glycol.

The mucosal compositions of this invention should also contain one or more water-soluble cellulose-derived polymers. Preferably, such polymers should be a cellulose gum such as one or more hydroxyalkylcellulose polymer. More preferably, the hydroxyalkylcellulose polymer should be one or more of hydroxyethylcellulose, hydroxymethylcellulose, hydroxypropylcellulose, hydroxypropylmethylcellulose and the like. Preferably, the cellulose-derived polymer should be present in the compositions of this invention in the amount of from about 0.1 to about 2% by weight of the composition.

The compositions of this invention intended for vaginal use may also contain one or more spermicides including but not limited to nonoxynol-9 and the like. Although such spermicides may be classified as surfactants, they generally have an HLB of less than 16 and are not useful as or in cleansing compositions and do not foam.

Preferably, an inorganic base may be used to adjust the pH of the composition to be compatible with the vaginal, oral or rectal mucosa. Potassium hydroxide or another alkali metal or alkaline earth metal base may be useful to provide the appropriate pH. Of course, any other physiological acceptable base may also be used in this manner. From about 0.05 to about 5% by weight inorganic base is preferably used.

The compositions of this invention may be prepared in accordance with those methods and processes known to those of skill in the art, or in accordance with the methods of preparation of this invention. For example, water-soluble components such as glycerin, propylene glycol, sorbitol, inorganic base, preservatives, and the like may be dissolved in water and to that combination cellulose-derived polymers may be added. Another method of preparation is mixing all the ingredients into a slurry without water, and then adding the slurry to water.

The composition is preferably substantially free of surfactant, including anionic, cationic, amphoteric, or nonionic surfactants.

Included in a liquid or lotion formation of the composition may be water, oils, preservatives, emulsifiers, viscosity enhancers, emollients, electrolytes, fragrance, buffers, pH modifiers, skin protectants, metal ion sequestrants and the like.

Wound Care Bandage

Absorbent articles such as bandages may also be used to cover the open wound and deliver a treatment solution containing the low MW HmP. In this invention, any absorbent bandage may used. Typically, bandages have three layers: a skin facing layer, and absorbent layer and a top layer which faces away from the user's skin. The bottom layer of the bandage is oriented toward the user's skin and may be made of an aperture film or other material that does not stick to the wound but allows the treatment solution to penetrate. The absorbent layer may be made of absorbent fibers and contains the treatment solution. The top layer may also be an aperture film. The top layer may have a smaller open area than the bottom layer; this will prevent undesirable escape of the treatment solution from the absorbent layer. The bandages may be square, rectangular, round, oval or triangle in shape. The bandages may vary generally will range from 0.25 mm to 5 mm thick.

Materials

Potassium Acrylates copolymer (Lubrizol, Wickliffe, Ohio) was supplied as a 30% active formulation. The solution was diluted to 0.5% active and 5% active in distilled water, phosphate buffer saline (PBS), or acrylates cross-polymer-4 (SF2). The following solutions were supplied at different concentrations and all were diluted to 0.5% active formulation in water. EDP200 Ureido acrylic/methacrylic acid copolymer (Rhodia, Aubervillier, Cedex) was supplied at 17.7% active formulation. EDP 300 Ureido N,N-dimethylacrylamide methacrylic acid copolymer (Rhodia, Aubervillier, Cedex) was supplied at 16.4% active formulation. Polyacrylate-33 (Rhodia, Cranbury, N.J.) was supplied at 29% active formulation. Acrylates Copolymer (Lubrizol, Wickliffe, Ohio) was supplied at 32% active formulation. Acrylates Copolymer (Lubrizol, Pedricktown, N.J.) was supplied at 30% active formulation. Inulin Lauryl Carbomate (Beneo-Bio Based Chemicals (Belgium) was supplied at 100% active formulation. Sodium Hydrolyzed Potato Starch Dodecenylsuccinate (Akzo Nobel, Salisbury, N.C.) was supplied at 100% active formulation. Octadecene/MA Copolymer (Chevron-Phillips, The Woodlands, Tex.) was supplied at a 2% active formulation. Subdilutions were further made in water or phosphate buffered saline (PBS)(Mattek, Ashland, Mass.) for the experiments.

EXAMPLE 1

Wound Healing Assay:

The wound healing experiment described below was used to evaluate the re-epithelialization properties of materials according to the invention. The experiment can also be used to determine collagen degradation of a formulation.

Full thickness skin equivalents were manufactured on a human collagen matrix plated with fibroblasts. Human keratinocytes were cultured on top of the collagen matrix and then brought out of the medium to produce a differentiated stratum corneum. Full thickness equivalents were manufactured and ordered from Mattek (Ashland, Mass.), and the medium was ordered to include extra growth factors. The medium was also supplemented with 2% human serum (Lonza, Gampel, Valais). The equivalents were received and cultured following manufacturer instructions. A 3 mm biopsy punch (Miltex, Plainsboro, N.J.) was made in the middle of the skin tissue equivalent, removing the epidermal layer but leaving the collagen layer intact. 6 µL of the surfactant solution was applied to area of the biopsy punch. The equivalents were cultured according to manufacturer's instructions for five days. On the fifth day, the cells were harvested and transferred to a 10% formalin buffered solution (VWR, Bridgeport, N.J.). The samples stained for Hematoxylin and eosin (H&E) staining (American Histolabs, Gaithersburg, Md.). The samples were scanned at 4× using an Olympus BH2 microscope with movable stage (Center Valley, Pa.). They were then analyzed using the Nikon imaging software (NIS) (Melville, N.Y.). Surface area and micron calculations were analyzed using the calibrated NIS software.

TABLE 1

Degradation of the collagen matrix measured by length of the collagen matrix in the middle of the wound bed.

| Material | INCI Name | Depth of the collagen matrix in the middle of the wound bed (µm) |
| --- | --- | --- |
| 0.5% active in PBS | Potassium Acrylates copolymer | 77.26 ± 15.28* |
| 0.5% active in Potassium Acrylates Crosspolymer-4 | Potassium Acrylates copolymer | 66.04 ± 14.79* |
| Vehicle control | Phosphate buffered saline | 421.50 ± 22.85 |
| Vehicle control | Acrylates Crosspolymer-4 | 414.94 ± 16.58 |

Numbers are reported ± SEM,
*p < 0.001 Compared by One Way ANOVA

Results 0.5% of active Potassium Acrylates copolymer caused significant degradation of the collagen matrix when tested in the wound healing model. Table 1 shows the depth of the collagen matrix measured in the middle of the wound bed. Potassium Acrylates copolymer was compared to another carbomer polymer, Acrylates Crosspolymer-4. Potassium Acrylates copolymer mixed with phosphate buffered saline (PBS) or Potassium Acrylates copolymer mixed with Acrylates Crosspolymer-4 caused significant degradation of the collagen matrix (p<0.001). Interestingly, only the collagen was degraded, the keratinocytes remained intact.

EXAMPLE 2

Gelatin Degradation Assay

Gelatin is an irreversibly hydrolyzed form of collagen and is therefore a good model of collagen hydrogels. This experiment examines how compositions according to the invention containing different concentrations of potassium acrylates copolymer liquefy gelatin over time.

A 2.5% (w/v) purified gelatin (Amresco, Solon, Ohio) was made in phosphate buffered saline (Mattek, Ashland, Mass.) and heated to 80° C. until melted. The solution was cooled and placed into either 6 well or 24 well plates. The solution solidified at room temperature for a minimum of 24 hours. After the solid gel had formed, 100 µL of the various compositions containing potassium acrylates copolymer were added to solidified gelatin. At different time points, the samples were aspirated and weighed on an analytical balance to measure the amount of liquefied gelatin. The aspirated amounts were pipetted back into the wells after weighing. The experiments were ended after no longer than 6 days.

To confirm that Potassium Acrylates copolymer can degrade collagen, dilutions of Potassium Acrylates copolymer were applied to a purified gelatin matrix. 100 µL of Potassium Acrylates copolymer was applied in different concentrations to the gelatin hydrogels, the amount of liquefied gelatin was measured 48 hours after application, shown in Table 2.

TABLE 2

Potassium Acrylates Copolymer shows a dose dependent increase in liquefied gelatin 48 hours after application.

| Material | Amount of liquefied gelatin (g) |
|---|---|
| Potassium Acrylates Copolymer 5% active in water | 0.2457 ± 0.0175** |
| Potassium Acrylates Copolymer 0.5% active in water | 0.1099 ± 0.0046** |
| Potassium Acrylates Copolymer 0.25% active in water | 0.0629 ± 0.0030** |
| Potassium Acrylates Copolymer 0.1% active in water | 0.0353 ± 0.0037* |
| Potassium Acrylates Copolymer 0.05% active in water | 0.0244 ± 0.0028 |
| Potassium Acrylates Copolymer 0.005% active in water | 0.0142 ± 0.0025 |
| Water | 0.0190 ± 0.0021 |

Numbers are reported ± SEM,
*$p = 0.05$ compared to Water,
**$p < 0.001$ compared to water analyzed by One Way ANOVA.

Potassium Acrylates copolymer caused a dose dependent degradation of collagen at 48 hours after application; Potassium Acrylates copolymer at 0.1% active formulation caused significantly more degradation of the gelatin matrix than water. This continued the trend as the concentration of Potassium Acrylates copolymer increased in solution.

The ability for a HMP to degrade a collagen matrix is a specialized function that is not identical to all HMPs. This ability most likely has to do with the size and shape of the HMPs.

For example, Potassium Acrylates polymer, a mild, hydrophobically modified polymer surfactant shows a surprising ability to degrade collagen effectively at a wide range of concentrations. This has a wide range of clinical applications from reducing keloid scarring to reduction of collagen implants.

What is claimed is:

1. A method of degrading collagen, comprising contacting collagen with a composition comprising at least one low molecular weight hydrophobically modified polymer in an amount effective to degrade said collagen wherein said hydrophobically modified low molecular weight polymer is potassium acrylates copolymer.

2. The method of claim 1, wherein said low molecular weight hydrophobically modified polymer is present in said composition in an amount of from about 0.1% to about 10% percent by weight of said composition.

3. The method of claim 1, wherein said low molecular weight hydrophobically modified polymer has a number average molecular weight of about 100,000 or less.

* * * * *